United States Patent
Hares

(10) Patent No.: US 11,083,534 B2
(45) Date of Patent: Aug. 10, 2021

(54) INSTRUMENT-ARM COMMUNICATIONS IN A SURGICAL ROBOTIC SYSTEM

(71) Applicant: CMR Surgical Limited, Cambridge (GB)

(72) Inventor: Luke David Ronald Hares, Cambridge (GB)

(73) Assignee: CMR Surgical Limited, Cambridge (GB)

( * ) Notice: Subject to any disclaimer, the term of this patent is extended or adjusted under 35 U.S.C. 154(b) by 61 days.

(21) Appl. No.: 15/621,524

(22) Filed: Jun. 13, 2017

(65) Prior Publication Data

US 2017/0360520 A1    Dec. 21, 2017

(30) Foreign Application Priority Data

Jun. 21, 2016  (GB) .................................... 1610839

(51) Int. Cl.
*G06F 17/00* (2019.01)
*A61B 34/00* (2016.01)
(Continued)

(52) U.S. Cl.
CPC .............. *A61B 34/74* (2016.02); *A61B 34/30* (2016.02); *A61B 34/35* (2016.02); *B25J 9/1689* (2013.01);
(Continued)

(58) Field of Classification Search
CPC ......... A61B 34/74; A61B 34/30; A61B 34/35; A61B 2034/305; A61B 2090/0808;
(Continued)

(56) References Cited

U.S. PATENT DOCUMENTS 5,868,803 A * 2/1999 Chen ................. H01L 21/67259
29/25.01
6,331,181 B1 12/2001 Tierney et al.
(Continued)

FOREIGN PATENT DOCUMENTS

CN   104640514 A    5/2015
EP   1962711      12/2001
(Continued)

OTHER PUBLICATIONS

Search Report related to priority application GB1610839.1, dated Dec. 15, 2016 (4 pgs.).
(Continued)

*Primary Examiner* — Ronnie M Mancho
(74) *Attorney, Agent, or Firm* — Renner, Otto, Boisselle & Sklar, LLP

(57) ABSTRACT

A surgical robot comprising a base and an arm extending from a proximal end attached to the base to a distal end attachable to a surgical instrument via a series of links interspersed by articulations. The arm comprises a receiver, a proximity sensor and a controller. The receiver is configured to receive data from the surgical instrument over a short-range wireless communications link with the surgical instrument. The proximity sensor is configured to detect the proximal presence of the surgical instrument. The controller is configured to respond to the proximity sensor detecting the proximal presence of the surgical instrument by enabling the short-range wireless communications link between the receiver and a transmitter of the surgical instrument to be established.

20 Claims, 10 Drawing Sheets

(51) Int. Cl.
*A61B 34/30* (2016.01)
*A61B 34/35* (2016.01)
*B25J 9/16* (2006.01)
*A61B 90/00* (2016.01)
*B25J 9/00* (2006.01)

(52) U.S. Cl.
CPC . *A61B 2034/305* (2016.02); *A61B 2090/0808* (2016.02); *B25J 9/0084* (2013.01)

(58) Field of Classification Search
CPC .... A61B 2562/08; A61B 90/90; B25J 9/1689; B25J 9/0084; B25J 5/02; B25J 5/0031; B25J 5/0056
USPC ......................................................... 700/245
See application file for complete search history.

(56) References Cited

U.S. PATENT DOCUMENTS

| | | | |
|---|---|---|---|
| 8,469,947 B2 | 6/2013 | Devengenzo et al. | |
| 9,566,122 B2 * | 2/2017 | Bowling | A61B 34/32 |
| 9,622,826 B2 * | 4/2017 | Diolaiti | A61B 34/30 |
| 9,919,424 B1 * | 3/2018 | Devengenzo | B25J 9/1656 |
| 10,011,018 B2 * | 7/2018 | McGrogan | A61B 90/50 |
| 10,335,151 B2 * | 7/2019 | Shelton, IV | A61B 17/105 |
| 2003/0070193 A1 * | 4/2003 | Pfeiffer | B25J 17/0208 |
| | | | 360/98.01 |
| 2006/0125806 A1 * | 6/2006 | Voyles | G06F 3/014 |
| | | | 345/184 |
| 2007/0119274 A1 * | 5/2007 | Devengenzo | A61B 34/30 |
| | | | 74/490.01 |
| 2008/0147089 A1 | 6/2008 | Loh et al. | |
| 2010/0026456 A1 | 2/2010 | Cline et al. | |
| 2011/0015521 A1 * | 1/2011 | Faul | A61N 5/1049 |
| | | | 600/426 |
| 2011/0218551 A1 * | 9/2011 | Devengenzo | A61B 34/30 |
| | | | 606/130 |
| 2011/0288573 A1 | 11/2011 | Yates et al. | |
| 2012/0143211 A1 * | 6/2012 | Kishi | A61B 34/30 |
| | | | 606/130 |
| 2012/0209291 A1 | 8/2012 | Anderson et al. | |
| 2013/0023860 A1 * | 1/2013 | Nagashimada | A61B 34/70 |
| | | | 606/1 |
| 2013/0204271 A1 | 8/2013 | Brisson et al. | |
| 2013/0324998 A1 * | 12/2013 | Kimball | A61B 17/320068 |
| | | | 606/41 |
| 2014/0081455 A1 * | 3/2014 | Goldberg | A61B 34/30 |
| | | | 700/250 |
| 2014/0171965 A1 | 6/2014 | Loh et al. | |
| 2014/0276949 A1 | 9/2014 | Staunton et al. | |
| 2015/0283704 A1 * | 10/2015 | Watanabe | B25J 9/1612 |
| | | | 700/259 |
| 2016/0250753 A1 * | 9/2016 | Yoshizawa | B25J 15/04 |
| | | | 700/258 |

FOREIGN PATENT DOCUMENTS

| | | |
|---|---|---|
| EP | 1439026 | 5/2007 |
| EP | 2772206 | 9/2014 |
| WO | 2010008126 | 1/2010 |
| WO | 2012018816 | 2/2012 |
| WO | 2013018926 | 2/2013 |
| WO | 2014043619 A1 | 3/2014 |
| WO | 2014071184 | 5/2014 |

OTHER PUBLICATIONS

International Search Report regarding PCT/GB2017/051776, dated Sep. 29, 2017 (6 pgs.).
First Office Action dated Dec. 17, 2020, for corresponding Chinese Patent Application No. 201780038463.9.
First Examination Report dated Apr. 30, 2021, for corresponding Indian Patent Application No. 201917002374.

* cited by examiner

INSTRUMENT-ARM COMMUNICATIONS IN A SURGICAL ROBOTIC SYSTEM

BACKGROUND

It is known to use robots for assisting and performing surgery. FIG. 1 illustrates a typical surgical robot 100 which consists of a base 108, an arm 102, and an instrument 105. The base supports the robot, and is itself attached rigidly to, for example, the operating theatre floor, the operating theatre ceiling or a trolley. The arm extends between the base and the instrument. The arm is articulated by means of multiple flexible joints 103 along its length, which are used to locate the surgical instrument in a desired location relative to the patient. The surgical instrument is attached to the distal end 104 of the robot arm. The surgical instrument penetrates the body of the patient 101 at a port 107 so as to access the surgical site. At its distal end, the instrument comprises an end effector 106 for engaging in a medical procedure.

FIG. 2 illustrates a typical surgical instrument 200 for performing robotic laparoscopic surgery. The surgical instrument comprises a base 201 by means of which the surgical instrument connects to the robot arm. A shaft 202 extends between base 201 and articulation 203. Articulation 203 terminates in an end effector 204. In FIG. 2, a pair of serrated jaws are illustrated as the end effector 204. The articulation 203 permits the end effector 204 to move relative to the shaft 202. It is desirable for at least two degrees of freedom to be provided to the motion of the end effector 204 by means of the articulation.

A surgeon utilises many instruments during the course of a typical laparoscopy operation. For this reason, it is desirable for the instruments to be detachable from and attachable to the end of the robot arm mid-operation. The controller of the robot arm needs to know which instrument is attached to the robot arm at any given time. It is known to electrically connect the instrument to the robot arm, and for the instrument to signal its identity to the robot arm via this electrical connection. The instrument has an interface which interfaces with the interface of the robot arm. In this case, the instrument interface has electrical contacts which connect to corresponding electrical contacts of the robot arm interface. The instrument thus signals its identity to the robot arm via the electrical interface.

To minimise risk of infection, operating theatres are sterile environments. Surgical instruments are sterilised between operations. However, the robot arms are not sterile. In order for a robot arm to be used in an operating theatre, a sterile barrier must be maintained between the robot arm and the rest of the operating theatre. To achieve this, the robot arm is covered in a sterile drape. The instrument attaches to the robot arm via an interface on the sterile drape. The sterile drape is a single use item that is disposed of after a single operation. Thus, it is desirable to minimise the cost of the sterile drape. For this reason, it is desirable to reduce the complexity of the sterile drape by eliminating the need to incorporate an electrical interfacing arrangement on it to interface the electrical contacts of the instrument interface to the electrical contacts of the robot arm interface.

SUMMARY OF THE INVENTION

According to an aspect of the invention, there is provided a surgical robot comprising: a base; and an arm extending from a proximal end attached to the base to a distal end attachable to a surgical instrument via a series of links interspersed by articulations, the arm comprising: a receiver configured to receive data from the surgical instrument over a short-range wireless communications link with the surgical instrument; and a proximity sensor configured to detect the proximal presence of the surgical instrument; and a controller configured to respond to the proximity sensor detecting the proximal presence of the surgical instrument by enabling the short-range wireless communications link between the receiver and a transmitter of the surgical instrument to be established.

The proximity sensor may comprise a Hall sensor.

The short-range wireless communications link may be a Near Field Communications link.

The data may be indicative of the value of one or more parameters of the instrument. These parameters may comprise a surgical instrument type, surgical instrument identity, surgical instrument usage data, and control data.

The surgical robot may further comprise a data store, and the surgical robot may be configured to receive data indicative of the surgical instrument identity; store the surgical instrument identity in the data store; subsequently receive a parameter update indicative of a surgical instrument identity and other parameter data; and only store the other parameter data of the parameter update if the surgical instrument identity of the parameter update matches the surgical instrument identity in the data store.

The receiver may be comprised within an arm transceiver, and the transmitter may be comprised within an instrument transceiver.

The controller may, in response to the short-range wireless communications link being established, control the arm transceiver to query the instrument transceiver over the short-range wireless communications link for the data.

The arm transceiver may periodically send data indicative of surgical instrument usage data to the instrument transceiver for storing in an instrument data store.

The data indicative of surgical instrument usage data may comprise data indicative of at least one of the total operation time of the surgical instrument, the number of uses of the surgical instrument, and the remaining lifetime of the surgical instrument.

The proximity sensor may detect that the surgical instrument has been detached from the arm, and the controller may respond to the detected detachment by controlling the arm transceiver to transmit data indicative of surgical instrument usage data to the instrument transceiver over the short-range wireless communications link.

The controller may only respond to the detected detachment by controlling the arm transceiver to transmit data indicative of surgical instrument usage data to the instrument transceiver over the short-range wireless communications link if the controller has not received a command indicating that the surgical instrument is to be detached from the arm.

The controller may prevent manipulation of the surgical instrument if the received data indicates that the instrument's lifetime has expired.

The arm may comprise a robot arm interface for mechanically interfacing a surgical instrument interface of the surgical instrument, and the proximity sensor may be located adjacent the robot arm interface.

The surgical robot may further comprise a surgical instrument, the surgical instrument comprising: a transmitter configured to transmit data over the short-range wireless communications link to the receiver; and a detectable tag configured to be detectable by the proximity sensor.

The detectable tag may be detectable by a Hall sensor.

The surgical instrument may further comprise a data store configured to store data indicative of surgical instrument usage data received from the arm transceiver.

The surgical instrument may comprise a surgical instrument interface for mechanically interfacing the robot arm interface, and the detectable tag may be located adjacent the surgical instrument interface proximal to the proximity sensor when the surgical instrument is attached to the arm.

According to a further aspect of the invention, there is provided a surgical robot comprising: a base; and an arm extending from a proximal end attached to the base to a distal end attachable to a surgical instrument via a series of links interspersed by articulations, the arm comprising: a receiver configured to receive data from the surgical instrument over a short-range wireless communications link with the surgical instrument; and a proximity sensor configured to detect the proximal presence of the surgical instrument; and a controller configured to respond to the receiver detecting a proximal transmitter operating according to the short-range wireless communications protocol and the proximity sensor not detecting the proximal presence of the surgical instrument by issuing an alert that the surgical instrument is not properly attached to the arm.

The controller may be further configured to respond to the receiver detecting a proximal transmitter operating according to the short-range wireless communications protocol and the proximity sensor not detecting the proximal presence of the surgical instrument by preventing manipulation of the surgical instrument.

BRIEF DESCRIPTION OF THE FIGURES

The present invention will now be described by way of example with reference to the accompanying drawings. In the drawings.

DETAILED DESCRIPTION

Figure 3:
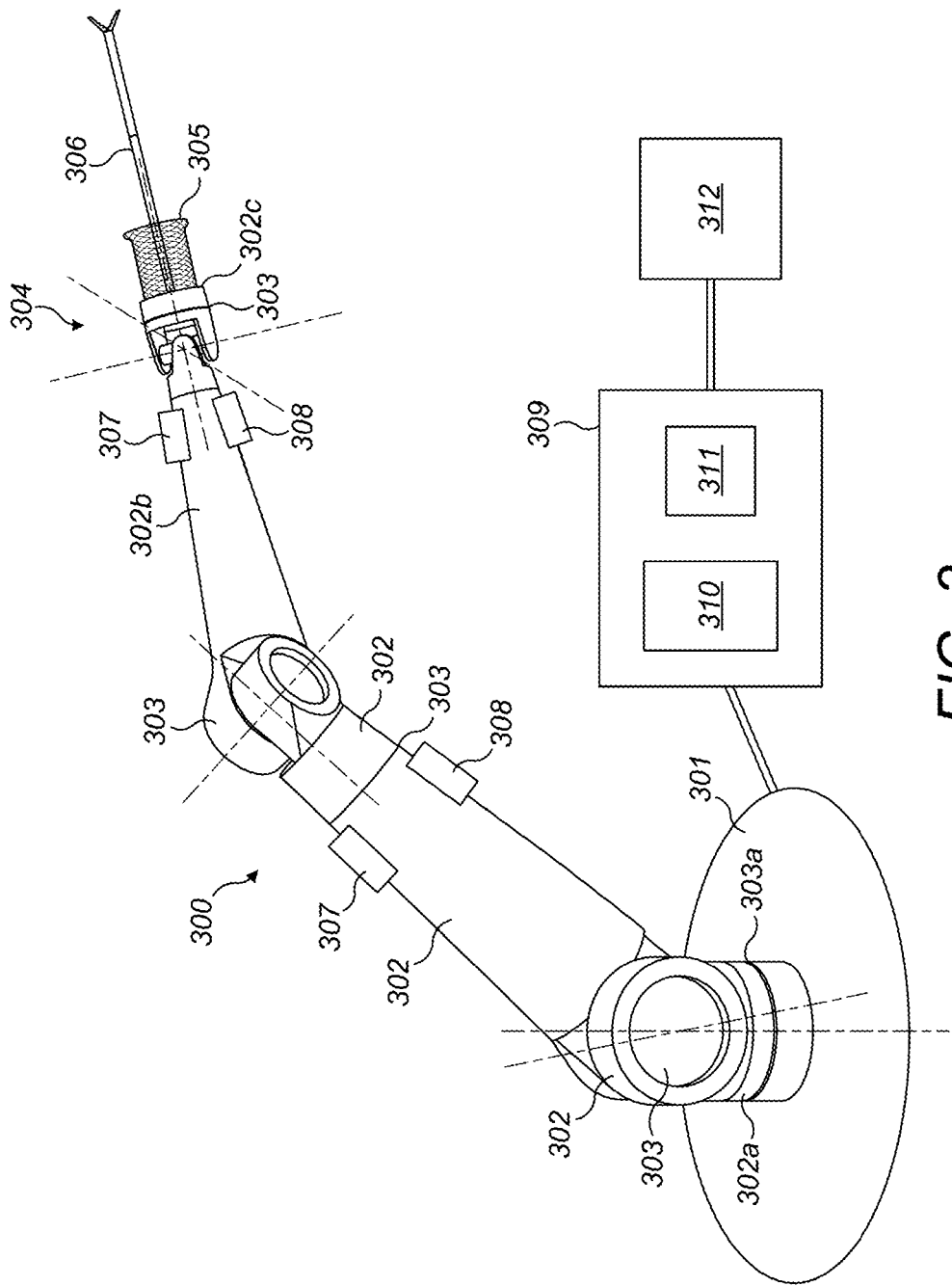
FIG. 3 illustrates a surgical robot.

FIG. 3 illustrates a surgical robot having an arm 300 which extends from a proximal end attached to a base 301. The arm comprises a number of rigid links 302. The links are coupled by revolute joints 303. The most proximal link 302a is coupled to the base by joint 303a. It and the other links are coupled in series by further ones of the joints 303. Suitably, a wrist 304 is made up of four individual revolute joints. The wrist 304 couples one link (302b) to the most distal link (302c) of the arm. The most distal link 302c is at the distal end of the arm and carries an attachment 305 for a surgical instrument 306. Each joint 303 of the arm has one or more motors 307 which can be operated to cause rotational motion at the respective joint, and one or more position and/or torque sensors 308 which provide information regarding the current configuration and/or load at that joint. Suitably, the motors are arranged proximally of the joints whose motion they drive, so as to improve weight distribution. For clarity, only some of the motors and sensors are shown in FIG. 3. The arm may be generally as described in our co-pending patent application PCT/GB2014/053523.

Figure 1:
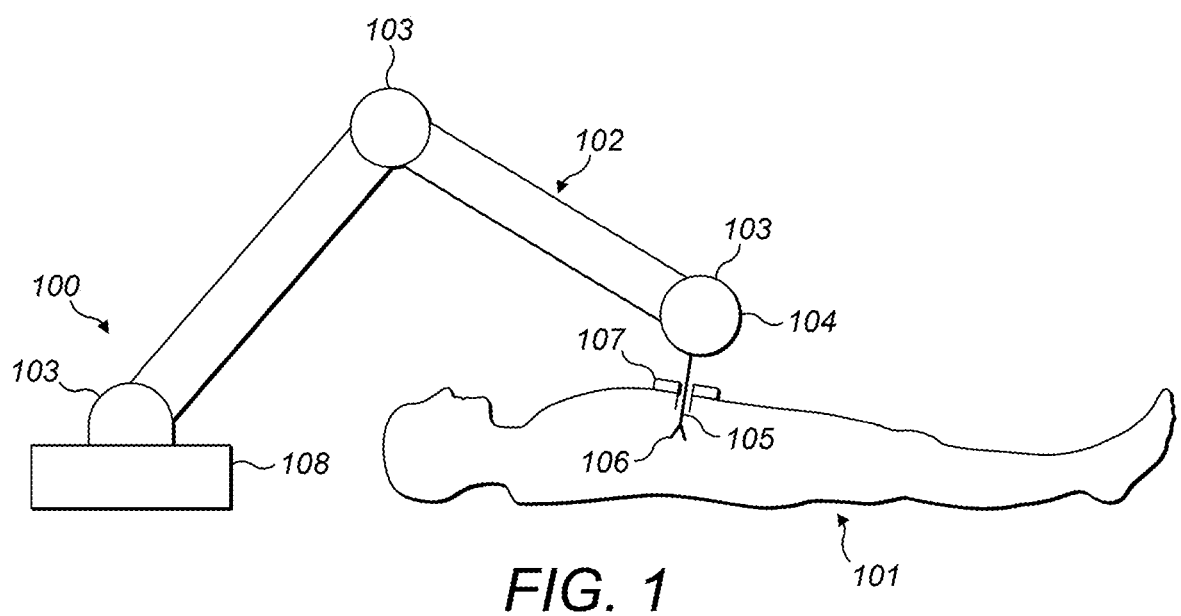
FIG. 1 illustrates a surgical robot performing a surgical procedure.
Figure 2:
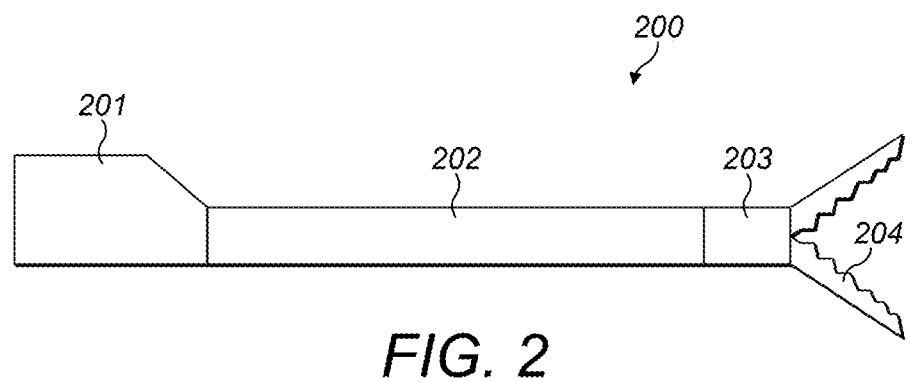
FIG. 2 illustrates a known surgical instrument.

The arm terminates in an attachment 305 for interfacing with the instrument 306. Suitably, the instrument 306 takes the form described with respect to FIG. 2. The attachment 305 comprises a drive assembly for driving articulation of the instrument. Movable interface elements of the drive assembly interface mechanically engage corresponding movable interface elements of the instrument interface in order to transfer drive from the robot arm to the instrument. One instrument is exchanged for another several times during a typical operation. Thus, the instrument is attachable and detachable from the robot arm during the operation. Features of the drive assembly interface and the instrument interface aid their alignment when brought into engagement with each other, so as to reduce the accuracy with which they need to be aligned by the user.

The instrument 306 comprises an end effector for performing an operation. The end effector may take any suitable form. For example, the end effector may be smooth jaws, serrated jaws, a gripper, a pair of shears, a needle for suturing, a camera, a laser, a knife, a stapler, a cauteriser, a suctioner. As described with respect to FIG. 2, the instrument comprises an articulation between the instrument shaft and the end effector. The articulation comprises several joints which permit the end effector to move relative to the shaft of the instrument. The joints in the articulation are actuated by driving elements, such as cables. These driving elements are secured at the other end of the instrument shaft to the interface elements of the instrument interface. Thus, the robot arm transfers drive to the end effector as follows: movement of a drive assembly interface element moves an instrument interface element which moves a driving element which moves a joint of the articulation which moves the end effector.

Controllers for the motors, torque sensors and encoders are distributed with the robot arm. The controllers are connected via a communication bus to control unit 309. A control unit 309 comprises a processor 310 and a memory 311. Memory 311 stores in a non-transient way software that is executable by the processor to control the operation of the motors 307 to cause the arm 300 to operate in the manner described herein. In particular, the software can control the processor 310 to cause the motors (for example via distributed controllers) to drive in dependence on inputs from the sensors 308 and from a surgeon command interface 312. The control unit 309 is coupled to the motors 307 for driving them in accordance with outputs generated by execution of the software. The control unit 309 is coupled to the sensors 308 for receiving sensed input from the sensors, and to the command interface 312 for receiving input from it. The respective couplings may, for example, each be electrical or optical cables, or may be provided by a wireless connection. The command interface 312 comprises one or more input devices whereby a user can request motion of the end effector in a desired way. The input devices could, for example, be manually operable mechanical input devices such as control handles or joysticks, or contactless input devices such as optical gesture sensors. The software stored in memory 311 is configured to respond to those inputs and cause the joints of the arm and instrument to move accordingly, in compliance with a pre-determined control strategy. The control strategy may include safety features which moderate the motion of the arm and instrument in response to command inputs. Thus, in summary, a surgeon at the command interface 312 can control the instrument 306 to move in such a way as to perform a desired surgical procedure. The control unit 309 and/or the command interface 312 may be remote from the arm 300.

Figure 4:
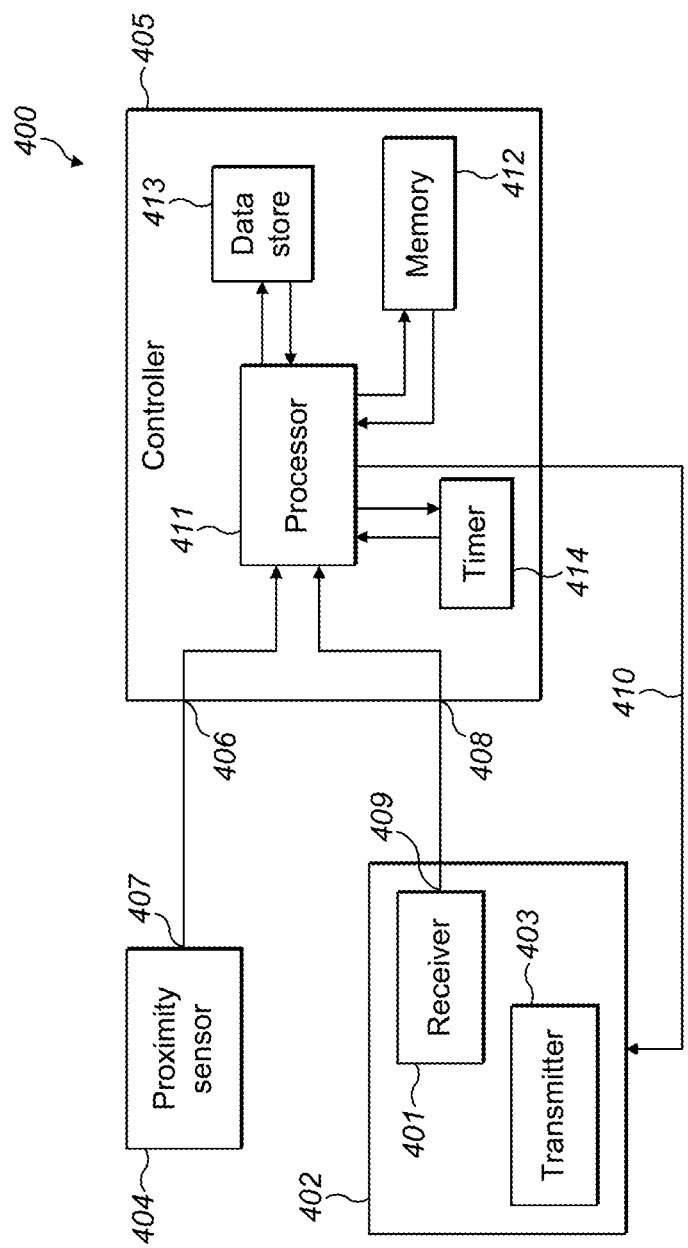
FIG. 4 illustrates schematically circuitry on the robot arm.
Figure 5:
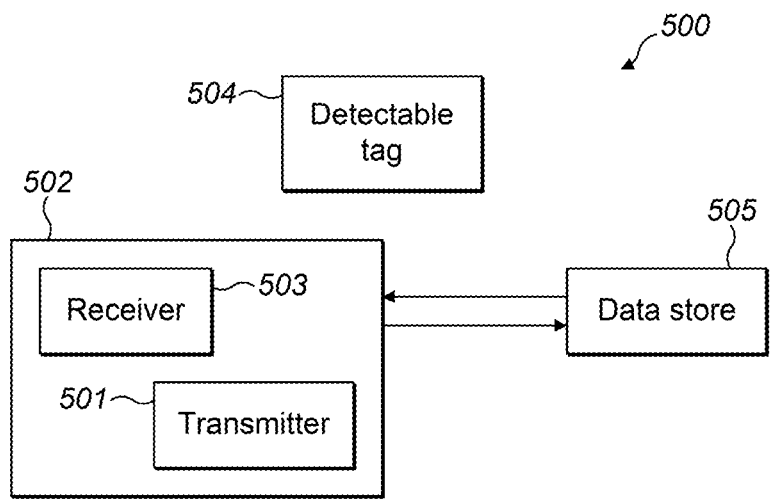
FIG. 5 illustrates schematically circuitry on the instrument.

FIG. 4 illustrates a schematic diagram of circuitry 400 on the robot arm 300 for detecting and communicating with the instrument 306. FIG. 5 illustrates a schematic diagram of circuitry 500 on the instrument 306 for communicating with the robot arm 300.

Instrument transmitter 501 is configured to transmit data to the robot arm 300. Arm receiver 401 is configured to receive the data transmitted from the instrument 306. This data is indicative of the value of one or more parameters of the instrument. These parameters include one, more or all of the following: instrument type, instrument identity, instrument usage data, and control data. The control data may include parameters of the robot arm drive assembly that the instrument is to adopt. The control data may include parameters of the instrument that the robot arm is to adopt. For example, the control data may include one, more or all of the following: the functions of the drive assembly interface elements, the functions of the instrument interface elements, the range of travel of the drive assembly interface elements including the maximum and minimum travels, the range of travel of the instrument interface elements including the maximum and minimum travels, the neutral/rest position of the drive assembly interface elements, the neutral/rest position of the instrument interface elements, the range of travel of the instrument joints including the maximum and minimum travels, and the neutral/rest position of the instrument joints. In one example, the data is a code. The code may be a number code. The value of one or more of the parameters of the instrument is embedded within the code. In other words, the value of the one or more parameters of the instrument are derivable from the code by analysing the code with an algorithm. In another example, the data itself includes the value of one or more of the parameters of the instrument. In either example, the data may be encrypted.

Instrument transmitter 501 and arm receiver 401 operate according to the same short-range wireless communications protocol. For example, they may operate according to an RFID (Radio Frequency Identification) protocol. In an exemplary implementation, they communicate according to a protocol that has a range of less than or the same as 4 cm. The protocol may have a range of less than or the same as 2 cm. The protocol may use NFC (Near Field Communication). Utilising a short-range wireless communications protocol as opposed to a wireless communications protocol that is not short-range reduces the likelihood of the instrument-arm communication interfering with other communication links in the operating theatre. It also reduces the likelihood of those other communication links interfering with the instrument-arm communication.

Instrument transmitter 501 may be comprised within a transceiver 502 which also comprises an instrument receiver 503. Arm receiver 401 may be comprised within a transceiver 402 which also comprises an arm transmitter 403. Arm transmitter 403 transmits data to the instrument 306, and instrument receiver 504 receives this data. The arm transmitter 403 and instrument receiver 503 operate according to the same short-range communications protocol as the instrument transmitter 501 and the arm receiver 401.

Using a wireless communications protocol allows the instrument 306 to communicate with the robot arm 300 without having to incorporate an electrical interfacing arrangement in the sterile drape which interposes the instrument and arm.

Some operations which it is envisaged may be performed by surgical robots require the use of two or more surgical instruments in close proximity to each other and hence two or more surgical robot arms in close proximity to each other. It is foreseeable that in utilising a short-range communications protocol as laid out above, one robot arm may be within range of an instrument attached to or being brought into attachment with another robot arm. This may lead to the robot arm receiving data indicative of the value of one or more parameters of an instrument not attached to it and/or an instrument receiving such data from a robot arm it is not attached to.

The robot arm circuitry of FIG. 4 additionally includes a proximity sensor 404. The instrument circuitry of FIG. 5 additionally includes a detectable tag 504. The detectable tag 504 is detectable by the proximity sensor 404. The proximity sensor 404 detects the proximal presence of the detectable tag 504. The proximity sensor has a shorter range than the wireless communications protocol of the arm receiver 401 and the instrument transmitter 501. The proximity sensor 404 may be one of a magnetic sensor such as a Hall sensor, a reed switch, an acoustic sensor, a capacitive sensor, an inductive sensor and an optical sensor.

In the example that the proximity sensor is a Hall sensor, the detectable tag 504 is a magnetic tag which is detectable by the Hall sensor. The Hall sensor senses a magnetic field in its vicinity. The Hall sensor detects the proximal presence of the magnetic tag when the magnetic flux density around the sensor exceeds a threshold. When the magnetic flux density around the sensor exceeds a threshold, the Hall sensor generates an output voltage.

The threshold and/or the internal amplification of the Hall sensor determine the range and sensitivity of the Hall sensor. The threshold and/or internal amplification of the Hall sensor and the strength of the magnetic tag may be predetermined to cause the Hall sensor (when located on the robot arm) to have the range and sensitivity required for its application.

For example, the threshold and/or internal amplification of the Hall sensor and the strength of the magnetic tag may be predetermined to cause the Hall sensor (when located on the robot arm) to detect a magnetic tag on an instrument which is attached to the robot arm, but not to detect a magnetic tag on an instrument attached to an adjacent robot arm. The threshold of the Hall sensor and the strength of the magnetic tag may both be predetermined to cause the Hall sensor (when located on the robot arm) to only detect the magnetic tag when the instrument is engaged with the robot arm. In this case, if the instrument interface is misaligned with the robot arm interface, or otherwise not properly docked to the robot arm interface, the Hall sensor does not sense the required threshold magnetic flux density, and hence does not generate the output voltage indicating that the magnetic tag has been detected.

In another example, the threshold and/or internal amplification of the Hall sensor and the strength of the magnetic tag may be predetermined to cause the Hall sensor (when located on the robot arm) to detect a magnetic tag on an instrument which is nearby but not necessarily attached to the robot arm. For example, the Hall sensor may detect the magnetic tag when they are separated by less than 10 cm. In response to this detection, the instrument may transmit data indicative of the value of one or more of its parameters (as described in more detail below). That data is processed by the controller which may output those parameter values to a user. In this way, the user may be informed of the parameter values before the instrument is docked on the robot arm. This gives the user the opportunity to not engage that specific instrument with the robot arm if any of the parameter values indicate that it is not appropriate for the operation, for example it is the wrong instrument type or does not have enough lifetime left to complete the operation.

The threshold of the Hall sensor and the strength of the magnetic tag are so as to cause the magnetic tag to be detected by the Hall sensor when the magnetic tag is less than 4 cm, preferably less than 1 cm, most preferably less than 1 mm from the Hall sensor.

The threshold and/or internal amplification of the Hall sensor and/or the strength of the magnetic tag may be dynamically adaptable to cause the Hall sensor (when located on the robot arm) to have the range and sensitivity required for its application. The range and sensitivity required may be different at different stages. For example, prior to engagement of the instrument and robot arm, it may be desirable for the Hall sensor to detect the magnetic tag when their separation is less than 10 cm, but once the instrument and robot arm are engaged, it may be desirable for the Hall sensor to detect the magnetic tag only when their separation is less than 1 mm. The threshold and/or internal amplification of the Hall sensor and/or the strength of the magnetic tag may be dynamically adaptable to change the range and sensitivity for these changing requirements during the duration of the operation.

Although described with respect to the Hall sensor and magnetic tag example, the above discussion of range and sensitivity applies to any combination of proximity sensor and detectable tag.

There may be two proximity sensors on the robot arm, a first which detects the detectable tag at a separation of less than 4 cm, and a second which detects the detectable tag at a separation of less than 1 mm. In this example, the first proximity sensor detects when the instrument is approaching engagement with the arm, and the second proximity sensor detects when the instrument is properly docked in the arm. If the first proximity sensor detects the detectable tag but the second proximity sensor does not detect the tag shortly after, then that is an indication that the instrument is between 1 mm and 4 cm away from a docked position on the robot arm. In other words, it is an indication that the instrument is not properly docked on the robot arm. For example, the instrument may be misaligned with the robot arm. The controller may respond to such a scenario by generating a warning signal. This warning signal may be output from the robot arm, for example as a warning light or warning sound. Alternatively, the warning signal may be transmitted to the surgeon console for output there, for example as a warning light or warning sound. Each of the two proximity sensors may be any one of those previously listed. The two proximity sensors may be of the same type, for example both Hall sensors. Alternatively, the two proximity sensors may be of different types, for example one a Hall sensor and one an optical sensor. The robot arm circuitry also comprises a controller 405. Controller 405 receives as an input 406 the output 407 of the proximity sensor 404. Thus, in the example above, the controller receives the output voltage signal of the Hall sensor. The controller also receives as an input 408 the output 409 of the receiver 401. The controller outputs control signal 410 to the arm receiver 401 and/or arm transmitter 403. The controller thereby controls the operation of the arm receiver 401 and/or the arm transmitter 403 in dependence on the output 407 of the proximity sensor.

Controller 405 comprises processor 411, memory 412 and data store 413. Memory 412 stores in a non-transient way software that is executable by the processor 411 to control the operation of the arm receiver 401 and/or the arm transmitter 403 to operate in the manner described herein. In particular, the software controls the processor 411 to cause the arm receiver to be enabled or disabled. The software may control the processor 411 to cause the arm transmitter to transmit data indicative of the value of one or more parameters of the instrument. For example, the software may control the processor 411 to cause the arm transmitter to transmit a code to the instrument. The software may control the processor 411 to generate and send alerts. These actions are controlled in response to the output of the proximity sensor 407, and/or the inputs from the sensors 308 and/or the surgeon command interface 312. Data store 413 may store parameter values of the instrument which the controller has derived from the data received from arm receiver 401. Data store 413 may store an indication of whether the instrument is docked in the arm or not as determined from the output of the proximity sensor 407. Data store 413 may be incorporated within memory 412. In this case, memory 412 is logically partitioned into a section for the data store 413 and a section for storing instructions for execution on processor 411. Data store 413 may be incorporated as registers in processor 411. Data store 413 may be one or more buffers.

The instrument circuitry also comprises a data store 505. Data store 505 stores data indicative of the values of one or more parameters of the instrument 306. This data may be a code as previously described. The data store 505 may store parameter values of the instrument. The data is retrieved from data store 505 to be transmitted by instrument transmitter 501.

The following describes several exemplary control methods which may be implemented using the circuitry described with respect to FIGS. 4 and 5.

Figure 6:
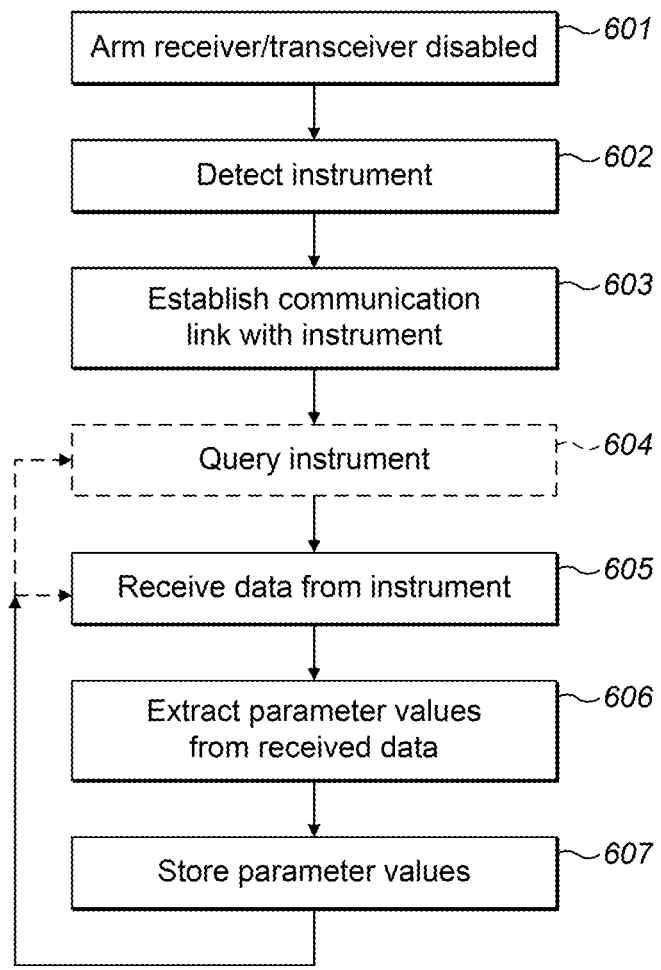
FIG. 6 is a flowchart illustrating a method of reading data from the instrument.

FIG. 6 illustrates a flowchart of a first control method. As shown at step 601, no communication link is initially established between an arm 300 and an instrument 306. The controller 405 may have disabled the arm receiver 401 or the arm transceiver 402 from communicating according to the short-range wireless communications protocol.

At step 602, the proximity sensor 404 detects the instrument and outputs a detection signal to the controller 405. The controller 405 stores an indication in the data store 413 that the instrument is docked in the robot arm.

At step 603, the controller responds to the detection signal by sending a control signal to the arm receiver 401 or arm transceiver 402 to enable a short-range wireless communications link to be established between the arm receiver 401 or arm transceiver 402 and the instrument transmitter 501 or instrument transceiver 502. For example, the control signal may switch the receiving function of the arm receiver 401 on, thereby enabling it to receive data transmitted by the instrument transmitter 501. Alternatively, or additionally, the control signal may cause the arm transmitter 403 to request a connection with the instrument receiver 503. Following this, a short-range wireless communications link is established between the arm and the instrument.

Once the communications link has been established, the controller 405 may, at step 604, control the arm transceiver 402 to transmit a query to the instrument. The query is a request for the instrument to provide parameter data. The request may be for one or more specific data parameters, such as the instrument's identity or instrument type. The request may be for an update of all the parameter data stored by the instrument. The instrument transceiver 502 receives the request from the arm transceiver 402.

In response to the request, the instrument transceiver 502 retrieves the data indicative of the requested parameter values from the data store 505 and transmits this data to the arm transceiver 402. In the example in which the instrument stores a code from which the requested parameter values are derivable, the instrument transceiver responds to the request by retrieving the code from data store 505 and transmitting this code to the arm transceiver. Suitably, the values of a plurality of different parameters are embedded within the same code. Suitably, the values of all of the requested parameter values are embedded within the same code. Thus, the instrument responds to a request for any one or any combination of parameter values by transmitting the same code. Alternatively, the instrument may store a plurality of codes, embedded in each of which is a different parameter value or set of parameter values. In this case, the instrument responds to a request for a parameter value or combination of parameter values by transmitting the code or codes in which are embedded the requested parameter values. Alternatively, the instrument may respond to any request for a parameter value or combination of parameter values by transmitting all the codes stored in the data store, in at least one of which is embedded the requested parameter value(s).

In the example in which the data stored by the instrument includes the parameter value(s) themselves, the instrument transceiver responds to the request by retrieving the requested parameter values from the data store and transmitting these parameter values to the arm transceiver. Alternatively, the instrument transceiver may respond to the request by retrieving all the parameter values stored in the data store and transmitting these to the arm transceiver.

The instrument transceiver may encrypt the data prior to sending it to the arm transceiver. Alternatively, the instrument may store the data in encrypted form in the data store, and then subsequently send the encrypted data. In either case, the encryption key is known to the robot arm controller 405.

At step 605, the arm transceiver 402 receives the data indicative of the requested parameter values from the instrument. At step 606, the controller 405 extracts the requested parameter values from the received data. The controller 405 decrypts the received data if it was encrypted. In the case that the received data is a code in which the parameter values are embedded, the controller inputs the code to an algorithm in order to determine the parameter values. The algorithm performs one or more functions on the code. Each function may determine one or more of the requested parameter values. The derived parameter values are then stored in data store 413 at step 607. In the case that the received data is the requested parameter values, these received parameter values are stored in data store 413.

The controller may cause the arm transceiver to query the instrument for a parameter data update at any time. The instrument responds as detailed above. This is illustrated in FIG. 6 by the control method looping from step 607 around to step 604.

Figure 7:
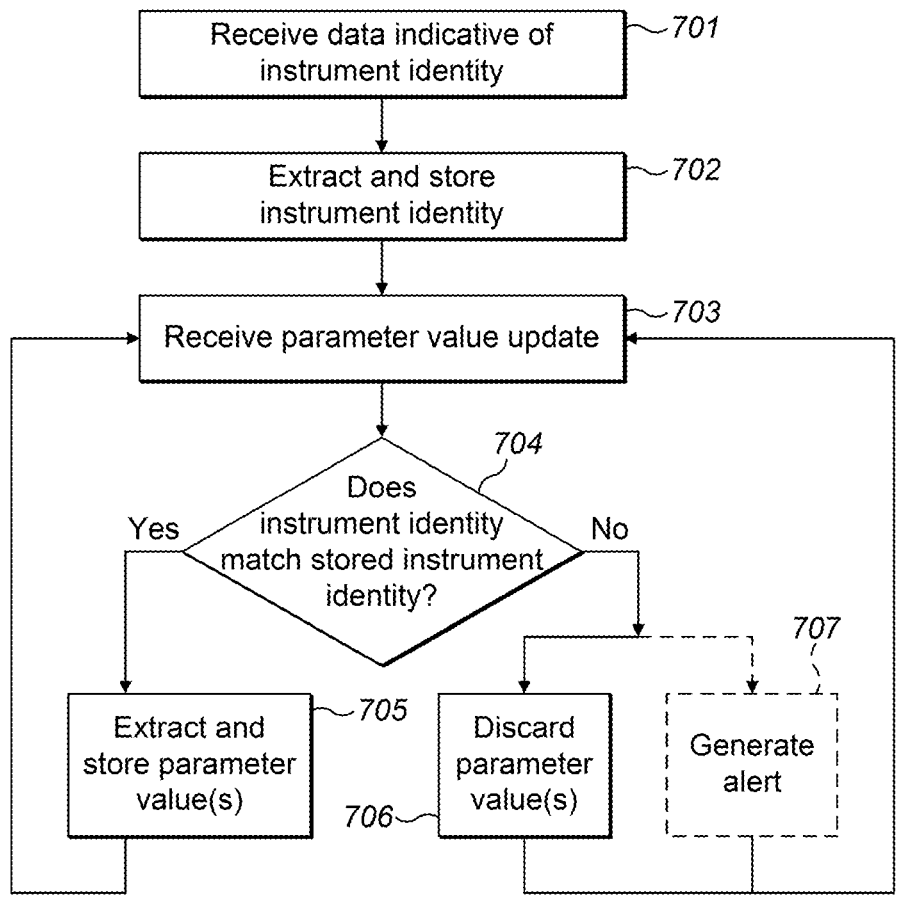
FIG. 7 is a flowchart illustrating a method of storing data from the instrument.

FIG. 7 illustrates a flowchart of a second control method. A communication link is established between the arm 300 and instrument 306. The instrument transmitter 501 extracts data indicative of the instrument identity from data store 505 and transmits this to the robot arm. At step 701, the arm receiver 401 receives the data indicative of the instrument identity from the instrument transmitter 501. The arm receiver 401 outputs the data indicative of the received instrument identity to the controller 405. The controller 405 receives the data indicative of the instrument identity from the arm receiver 401. The controller extracts the instrument identity from the data indicative of the instrument identity as described with respect to FIG. 6, and stores the instrument identity in data store 413 at step 702.

Subsequently, at step 703, the arm receiver 401 receives a parameter value update. The parameter value update comprises data indicative of an instrument identity and other parameter value(s). The arm receiver 401 outputs the received parameter value update to the controller 405. The processor 411 receives the parameter value update, and extracts the instrument identity from the parameter value update as in step 701. The processor 411 reads the stored instrument identity from data store 413. Processor 411 compares the instrument identity from the parameter value update to the stored instrument identity at step 704. If the instrument identity from the parameter value update matches the stored instrument identity, then at step 705, the processor extracts the other parameter value or parameter values from the parameter value update and stores those parameter values in the data store 413. The processor may also send the parameter values to control unit 309. Control unit 309 may send one or more of these parameter values to the surgeon command interface 312. The parameter values may be displayed to the surgeon. If the instrument identity from the parameter value update does not match the stored instrument identity, then at step 706 the processor discards the parameter value(s) in the parameter value update. Optionally, at step 707, the processor generates an alert. This alert may be sent to the control unit 309. The control unit 309 may generate an alert on the surgeon command interface 312. For example, an alert may be displayed to the surgeon. Following step 705, the method returns to step 703 where the arm receives another parameter value update. Following step 706, the method returns to step 703 where the arm receives another parameter value update.

Thus, once an instrument has registered its identity with the robot arm via steps 701 and 702, the controller 405 only stores parameter values received from an instrument having that instrument identity. Thus, even if the arm receiver 401 is within communications range of another instrument which is not attached to the arm, and receives parameter values from that other instrument, the controller does not store these parameter values because the instrument identity associated with those parameter values does not match the instrument identity of the attached instrument stored in data store 413.

Figure 8:
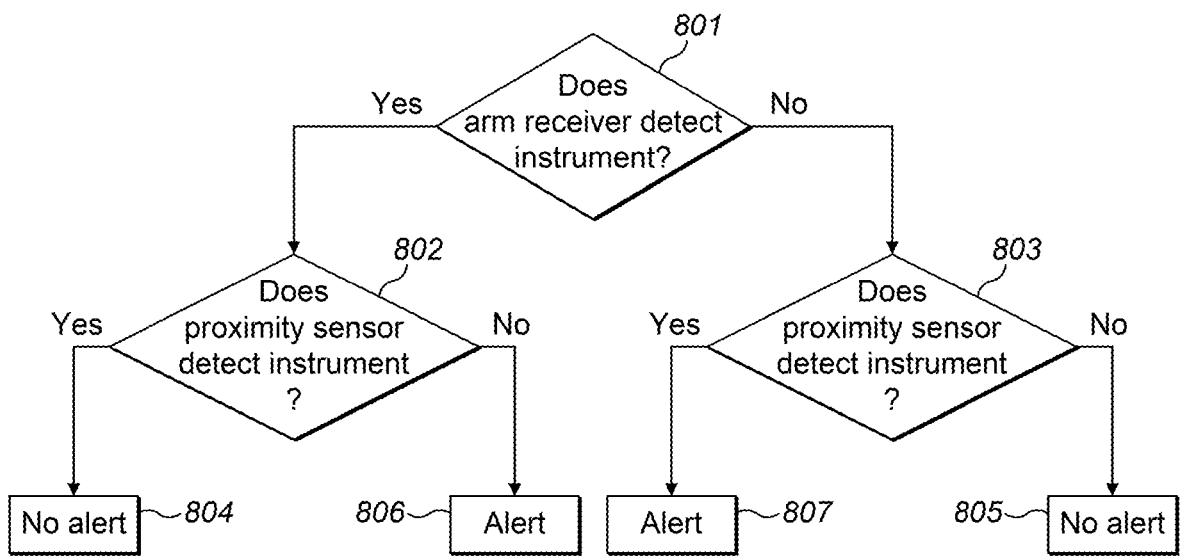
FIG. 8 is a flowchart illustrating a method of detecting a sensor malfunction.

FIG. 8 illustrates a flowchart of a third control method. The arm receiver 401 is operational to receive connection requests and public broadcasts according to its short-range wireless communications protocol. In this way, the arm receiver 401 detects a proximal transmitter operating according to the same short-range wireless communications protocol. In other words, in this way, the arm receiver 401 detects a nearby instrument. Meanwhile, the proximity sensor 404 is operating in a mode in which it only detects the instrument if the instrument is properly docked in the robot arm.

At step 801, processor 411 analyses the signal output from the arm receiver 401 to determine if the arm receiver 401 detects a nearby instrument. Whether the arm receiver 401 has detected a nearby instrument or not, the processor 411 goes on to, at steps 802 and 803, analyse the signal output from the proximity sensor 404 to determine if the proximity sensor 404 has detected an instrument. The processor 411 may, alternatively, analyse the output from the proximity sensor prior to analysing the output from the arm receiver. In other words, the processor 411 may perform steps 802/803 prior to step 801.

If the processor 411 determines that the arm receiver 401 has detected an instrument and the proximity sensor 404 has also detected an instrument, then the processor does not generate an alert at step 804. If the processor 411 determines that the arm receiver 401 has not detected an instrument and the proximity sensor 404 has also not detected an instrument, then the processor does not generate an alert at step 805.

If the processor 411 determines that the arm receiver 401 has detected an instrument but the proximity sensor 404 has not detected an instrument, then the processor generates an alert at step 806. If the processor 411 determines that the arm receiver 401 has not detected an instrument but the proximity sensor 404 has detected an instrument, then the processor generates an alert at step 807. In both cases, the controller 405 sends the alert to control unit 309 which may then alert the surgeon command interface 312. The alert may indicate a malfunction. This malfunction may be that the instrument has not properly docked in the robot arm. Alternatively the malfunction may be that the proximity sensor has failed. The controller 405 or control unit 309 may additionally respond to only one of the arm receiver and proximity sensor detecting an instrument by preventing manipulation of the surgical instrument. The controller 405 or control unit 309 may do this by disengaging robotic control of the surgical instrument by the surgeon command interface 312.

When a Hall sensor fails, it may generate an output voltage in the absence of a magnetic field or it may not generate an output voltage in the presence of a magnetic field. To avoid inaccurate sensing, two Hall sensors can be used. If the two Hall sensors read differently, then that is an indication that one of them is faulty. However, in this method, since the arm receiver 401 also detects a nearby instrument, only one Hall sensor need be used since a fault in the Hall sensor is detectable by the arm receiver 401.

FIGS. 9a, 9b, 9c and 9d all illustrates flowcharts of control methods for recording surgical instrument usage data. Surgical instruments are generally multiple-use implements. They are sterilised between operations and re-used. However, they do have a lifetime beyond which they are not suitable for use. Thus, it is useful for data indicative of the usage of the surgical instrument to be stored at the instrument. A communication link is established between the arm 300 and instrument 306.

Figure 9A:
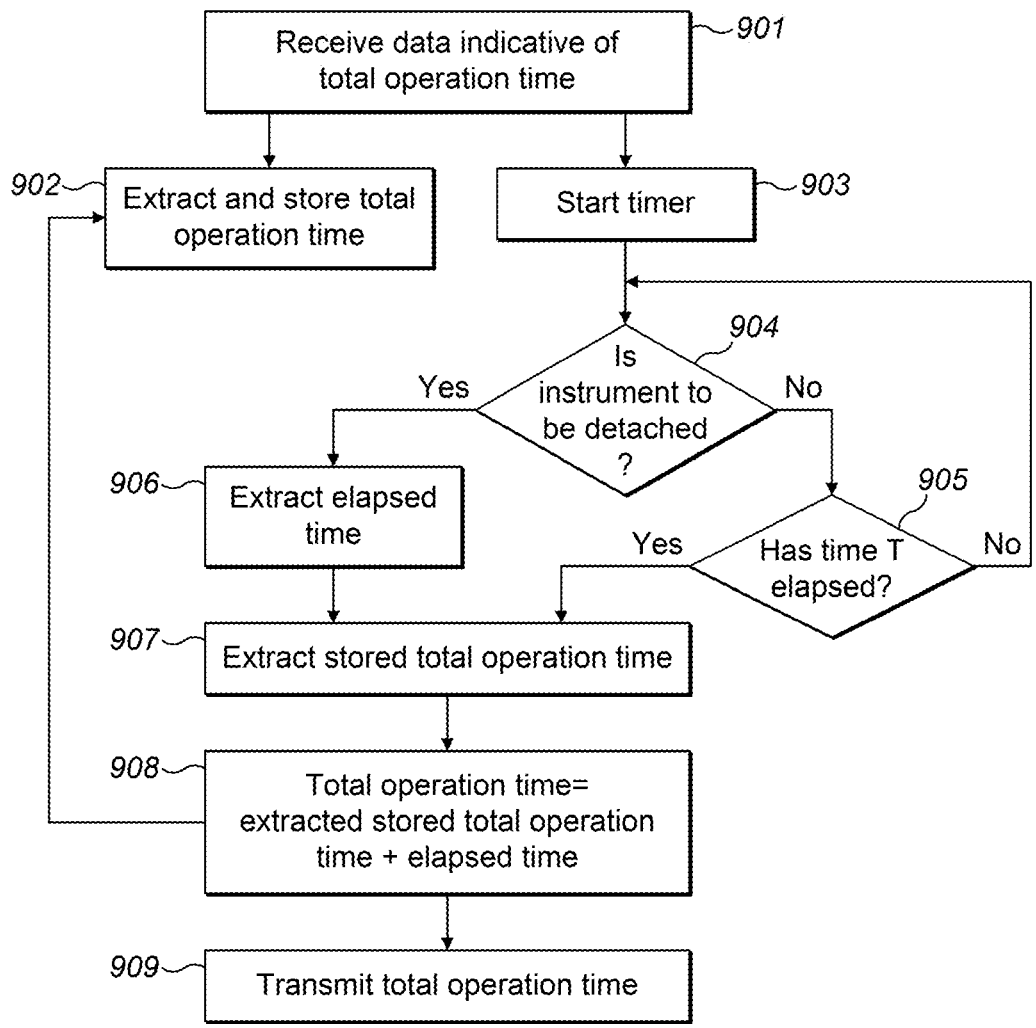
FIGS. 9a, 9b, 9c and 9d all illustrate flowcharts of control methods for recording surgical instrument usage data.

In FIG. 9a, the instrument transmitter 501 extracts data indicative of the total operation time of the surgical instrument from data store 505 and transmits this to the robot arm. At step 901, the arm receiver 401 receives the data indicative of the total operation time from the instrument transmitter 501. The arm receiver 401 outputs this data to the controller 405. The controller 405 receives this data from the arm receiver 401. The controller 405 extracts the total operation time from the data indicative of the total operation time as described with respect to FIG. 6. The controller 405 then stores the total operation time in data store 413 at step 902.

The controller 405 also comprises a timer 414. Timer 414 operates under the control of processor 411. The processor 411 responds to receiving the data indicative of the total operation time from the arm receiver 401 by controlling the timer 414 to start timing at step 903. The controller then operates a control loop. The controller determines if it has received a command that the instrument is to be detached at step 904. If it has not received such a command then it queries the timer 414 at step 905 to see if a time T has elapsed since the timer was started. If the result of the query is that a time T has not elapsed, then the control loop returns to step 904 where the controller determines if the instrument is to be detached. If the instrument is to be detached, then the processor 411 extracts the elapsed time since the timer was started from the timer in step 906. If either the instrument is to be detached or the time T has elapsed, then the processor extracts the stored total operation time from the data store 413 at step 907. At step 908, the processor determines the total operation time. The total operation time is the stored total operation time plus the elapsed time. The processor then writes this total operation time to the data store 413. The processor 414 may also control the arm transmitter 403 to transmit data indicative of the total operation time at step 909. This data may be a code, embedded in which is the total operation time. For example, the code may be a number code. Alternatively, the data indicative of the total operation time may include the total operation time. The data may be encrypted prior to transmission. The arm transmitter 403 transmits the data indicative of the total operation time. The instrument receiver receives the data indicative of the total operation time and stores this in data store 505.

The controller 405 may store a predetermined maximum operation time for the surgical instrument. On extracting the total operation time at step 902, the processor 411 may compare the total operation time to the maximum operation time. If the total operation time exceeds the maximum operation time, the processor 411 may generate an alert. If the total operation time is within a time T' of the maximum operation time, the processor may generate an alert. In either case, the alert is sent to the control unit 309. The control unit 309 may alert the surgeon command interface 312. In addition to the alert, either the controller 405 or the control unit 309 may prevent manipulation of the surgical instrument.

Figure 9B:
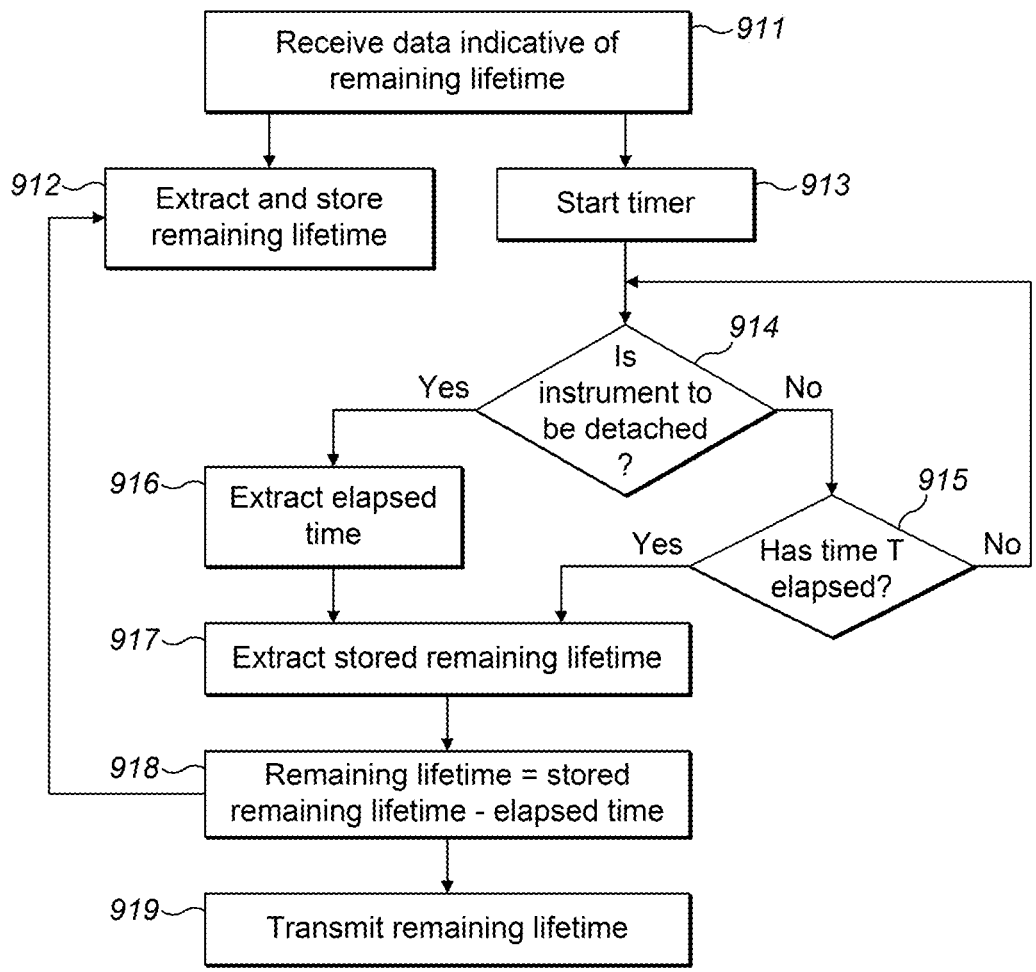

In FIG. 9b, the instrument transmitter 501 extracts data indicative of the remaining lifetime of the surgical instrument from data store 505 and transmits this to the robot arm. At step 911, the arm receiver 401 receives the data indicative of the remaining lifetime from the instrument transmitter 501. The arm receiver 401 outputs this data to the controller 405. The controller 405 receives this data from the arm receiver 401. The controller 405 extracts the total operation time from the data indicative of the remaining lifetime as described with respect to FIG. 6. The controller 405 then stores the total operation time in data store 413 at step 912.

The processor 411 responds to receiving the data indicative of the remaining lifetime from the arm receiver 401 by controlling the timer 414 to start timing at step 913. The controller then operates a control loop. The controller determines if it has received a command that the instrument is to be detached at step 914. If it has not received such a command then it queries the timer 414 at step 915 to see if a time T has elapsed since the timer was started. If the result of the query is that a time T has not elapsed, then the control loop returns to step 914 where the controller determines if the instrument is to be detached. If the instrument is to be detached, then the processor 411 extracts the elapsed time since the timer was started from the timer in step 906. If either the instrument is to be detached or the time T has elapsed, then the processor extracts the stored remaining lifetime from the data store 413 at step 917. At step 918, the processor determines the remaining lifetime. The remaining lifetime is the stored remaining lifetime minus the elapsed time. The processor then writes this remaining lifetime to the data store 413. The processor 414 may also control the arm transmitter 403 to transmit data indicative of the remaining lifetime at step 919. This data may be a code, embedded in which is the remaining lifetime. For example, the code may be a number code. Alternatively, the data indicative of the remaining lifetime may include the remaining lifetime. The data may be encrypted prior to transmission. The arm transmitter transmits the data indicative of the remaining lifetime. The instrument receiver receives the data indicative of the remaining lifetime and stores this in data store 505.

On extracting the remaining lifetime at step 912, the processor 411 may compare the remaining lifetime to 0. If the remaining lifetime is less than or the same as zero, the processor 411 may generate an alert. If the remaining lifetime is within a time T' of 0, the processor may generate an alert. In either case, the alert is sent to the control unit 309. The control unit 309 may alert the surgeon command interface 312. In addition to the alert, either the controller 405 or the control unit 309 may prevent manipulation of the surgical instrument.

The controller may cause the arm transmitter to periodically transmit data indicative of usage data to the instrument. For example, the controller may cause the arm transmitter to transmit this data every 30 seconds, or every minute, or every 5 minutes. The controller may additionally cause data to be transmitted to the instrument at any time. For example, the controller may cause data indicative of usage data to be transmitted to the instrument in response to receiving a command to do so from the control unit 309.

Figure 9C:
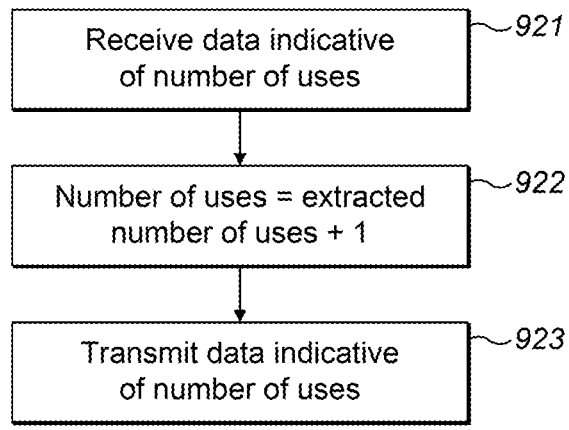

In FIG. 9c, the instrument transmitter 501 extracts data indicative of the number of uses of the surgical instrument from data store 505 and transmits this to the robot arm. At step 921, the arm receiver 401 receives the data indicative of the number of uses from the instrument transmitter 501. The arm receiver 401 outputs this data to the controller 405. The controller 405 receives this data from the arm receiver 401. The controller 405 extracts the number of uses from the data indicative of the number of uses as described with respect to FIG. 6.

The processor generates the number of uses to be the extracted number of uses plus 1. The processor then controls the transmitter 403 to transmit data indicative of the number of uses to the instrument. This data may be a code, embedded in which is the number of uses. For example, the code may be a number code. Alternatively, the data indicative of the number of uses may include the number of uses. The data may be encrypted prior to transmission. The arm transmitter 403 transmits the data indicative of the number of uses. The instrument receiver receives the data indicative of the number of uses and stores this in data store 505. The processor 411 may additionally store the number of uses in the data store 413.

The controller 405 may store a predetermined maximum number of uses for the surgical instrument. On extracting the number of uses at step 922, the processor 411 may compare the number of uses to the maximum number of uses. If the number of uses is the same as or exceeds the maximum number of uses, the processor 411 may generate an alert. The alert is sent to the control unit 309. The control unit 309 may alert the surgeon command interface 312. In addition to the alert, either the controller 405 or the control unit 309 may prevent manipulation of the surgical instrument.

Figure 9D:
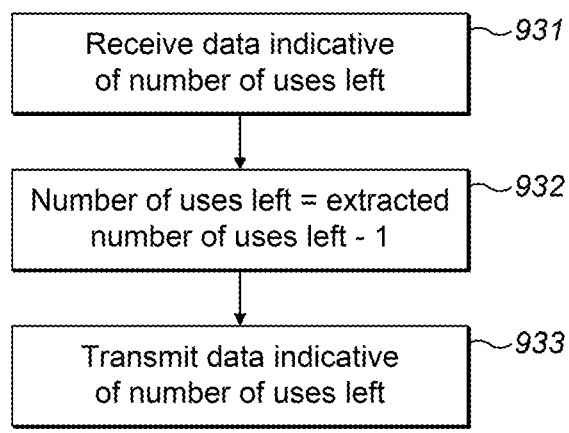

If FIG. 9d, the instrument transmitter 501 extracts data indicative of the number of uses left of the surgical instrument from data store 505 and transmits this to the robot arm.

At step 931, the arm receiver 401 receives the data indicative of the number of uses left from the instrument transmitter 501. The arm receiver 401 outputs this data to the controller 405. The controller 405 receives this data from the arm receiver 401. The controller 405 extracts the number of uses left from the data indicative of the number of uses left as described with respect to FIG. 6.

The processor generates the number of uses left to be the extracted number of uses left minus 1. The processor then controls the transmitter 403 to transmit data indicative of the number of uses left to the instrument. This data may be a code, embedded in which is the number of uses left. For example, the code may be a number code. Alternatively, the data indicative of the number of uses left may include the number of uses left. The data may be encrypted prior to transmission. The arm transmitter 403 transmits the data indicative of the number of uses left. The instrument receiver receives the data indicative of the number of uses left and stores this in data store 505. The processor 411 may additionally store the number of uses left in the data store 413.

On extracting the number of uses left at step 932, the processor 411 may compare the number of uses left to 0. If the number of uses left is the same as or less than 0, the processor 411 may generate an alert. The alert is sent to the control unit 309. The control unit 309 may alert the surgeon command interface 312. In addition to the alert, either the controller 405 or the control unit 309 may prevent manipulation of the surgical instrument.

The control methods described with respect to FIGS. 9a, 9b, 9c and 9d may be used together in any combination. The arm receiver 401 may receive data indicative of any combination of the following: total operation time, remaining lifetime, number of uses, and number of uses left. For example, the arm receiver 401 may receive a code in which is embedded a combination of the values of the listed usage data parameters. The controller 405 may then perform the corresponding methods described in FIG. 9 for those usage data parameter values. For example, the controller may determine that the surgical instrument has a remaining lifetime of 1 hour and 2 uses left. The controller may then issue an alert if any one of the determined usage data parameter values will expire before the end of the scheduled operation. In the example above, the controller would issue an alert if the operation was scheduled to take longer than 1 hour even through the surgical instrument still has 2 uses left.

The robot arm may check the usage data of the instrument prior to the instrument being attached to the robot arm. The operator may bring the instrument within range of the short-range communications protocol to the robot arm, without mounting the instrument on the arm. For example, there may be an arm receiver located towards the base of the robot arm that the operator brings the instrument within range of. The instrument may be in sterile packaging at this time. The instrument transmits data indicative of usage data to the robot arm. The robot arm receives the transmitted data. The processor extracts and analyses the usage data as described above. If the usage data indicates that the lifetime of the instrument has expired or that there is insufficient lifetime left to last for the operation, the processor issues an alert. The alert may be in the form of an indicator on the arm. For example a light or noise on the arm. In addition to the alert, the controller may also prevent the instrument from being mounted on the robot arm. For example, the controller may prevent the interface of the robot arm from being placed into an engageable configuration with the instrument.

The usage data may be checked as described in the previous paragraph by a device other than the robot arm. For example a receiver operating according to the short-range communications protocol may be located on an instrument storage rack, or may be a hand-held reader. Since the receiver does not need to be in contact with the instrument in order to read the usage data, a non-sterile reader comprising the receiver can be used to read usage data from a sterile instrument. For example, during an operation, a technician could use such a reader to read the instrument type of an instrument currently in use on the robot arm (using the methods described herein), and then go to an instrument storage rack and use the reader (using the methods described herein) to locate another instrument of the same instrument type for use in the operation. Such a reader, which also incorporates a transmitter which operates according to the short-range communications protocol, could be used during the production process of the instrument. Once the instrument has been produced and packaged in sterile packaging, an instrument identity could be written to the instrument wirelessly from the transmitter of the reader according to the short-range communications protocol.

Figure 10:
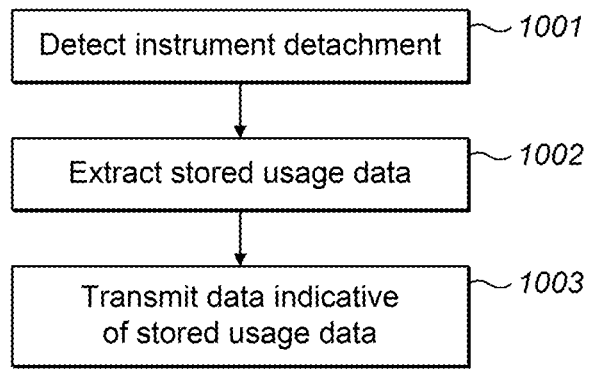
FIG. 10 illustrates a method of writing data to an instrument.

FIG. 10 illustrates a flowchart of a further control method. A communication link is initially established between an arm 300 and an instrument 306. At step 1001, the proximity sensor 404 detects the instrument has been detached from the robot arm and outputs a signal to the controller 405 accordingly. The processor 411 receives the signal from the proximity sensor 404 indicating that the instrument has been detached from the robot arm. The processor responds by extracting usage data of the surgical instrument from the data store 413 at step 1002. The processor generates data indicative of the extracted usage data. The processor may encrypt this data. The processor outputs the data to the arm transmitter 403 and controls the arm transmitter 403 to transmit the data to the instrument. The arm transmitter 403 transmits the data to the instrument at step 1003 over the short-range wireless communications link. The instrument receiver 503 receives the data and writes is to data store 505.

After detecting that the instrument has been detached at step 1001, the controller 405 may determine if it has received a command indicating that the surgical instrument is to be detached from the robot arm. If this command has been received, the controller may then determine if it has already controlled the arm transmitter to transmit data indicative of the usage data to the instrument in response to the command. If it has already sent data indicative of the usage data, then the controller may not perform steps 1002 and 1003 of FIG. 10.

This method ensures that data indicative of the usage data is written to the instrument even if the instrument is removed from the robot arm without warning. Since the arm transceiver 402 and instrument transceiver 502 communicate wirelessly, the robot arm does not need to be in contact with the instrument in order to transmit the data indicative of the usage data to the instrument. Thus, an attempt to fraudulently prevent data indicative of the usage data from being written to the instrument by removing it without informing the robot arm will fail because the robot arm responds by immediately writing the data indicative of the usage data to the instrument using the short-range wireless communications link.

Figure 11:
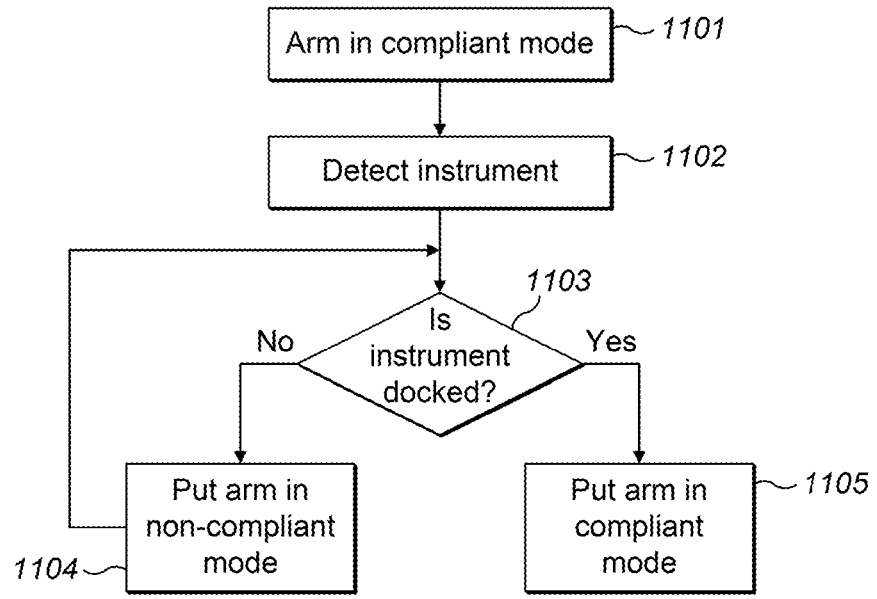
FIG. 11 illustrates a method of changing the mode of a robot arm.

FIG. 11 illustrates a control method for changing the mode of a robot arm. At step 1101, the robot arm is initially in a compliant mode. In a compliant mode, the robot arm responds to some external forces by driving the motors to move the joints in the direction of the force. Thus, for example, the robot arm may respond to a person pushing the elbow joint of the robot arm by causing the elbow joint to move in the direction it was pushed. In a non-compliant mode, the robot arm does not respond to external forces by causing the robot arm to move.

At step 1102, the arm receiver 401 detects a nearby instrument in the manner previously described. The arm receiver 401 outputs this detection to the controller 405. The controller 405 responds by determining whether the instrument is docked in the robot arm at step 1103. The controller 405 may store an indication of whether the instrument is docked in the data store 413. Alternatively, the controller may query the control unit 309 to determine whether the instrument is docked. Either from the data store 413, or the control unit 309, the controller 405 receives an indication of whether the instrument is docked in the robot arm. If the instrument is not docked in the robot arm, the controller 405 changes the operational mode of the robot arm to a non-compliant mode at step 1104. The method then returns to step 1103. Once the controller has determined that the instrument is docked, it changes the operational mode of the robot arm back to compliant mode at step 1105.

This method changes the robot arm to a non-compliant mode whilst an instrument is being connected to the robot arm. Thus, the robot arm is rigid as the instrument is being mounted to the robot arm, which makes it easier for a person to properly dock the instrument.

Whilst an instrument is docked to the robot arm, the arm receiver 401 may detect another instrument. Since an instrument is already docked in the arm, the controller determines that an instrument is already docked at step 1103, and hence leaves the robot arm in the compliant mode. Thus, sensing an additional instrument does not cause the controller to change the robot arm to a non-compliant mode.

Two different robot arms may detect the same instrument at step 1102. If this happens, the control unit 309 determines which robot arm the instrument is to be docked with, and causes only that robot arm to be put in a non-compliant mode at step 1104. The control unit 309 may do this by determining which robot arm is receiving the strongest signal over the communications link, and select that robot arm to be the one which is put in the non-compliant mode.

FIGS. 6 to 11 all illustrate flowcharts for control methods. It will be understood that the steps may be performed in a different order to that shown. Some steps may be omitted.

The control methods of FIGS. 6 to 11 have been described as being implemented by the controller 405. Alternatively, control unit 309 or a combination of control unit 309 and controller 405 may perform these control methods.

Figure 12:
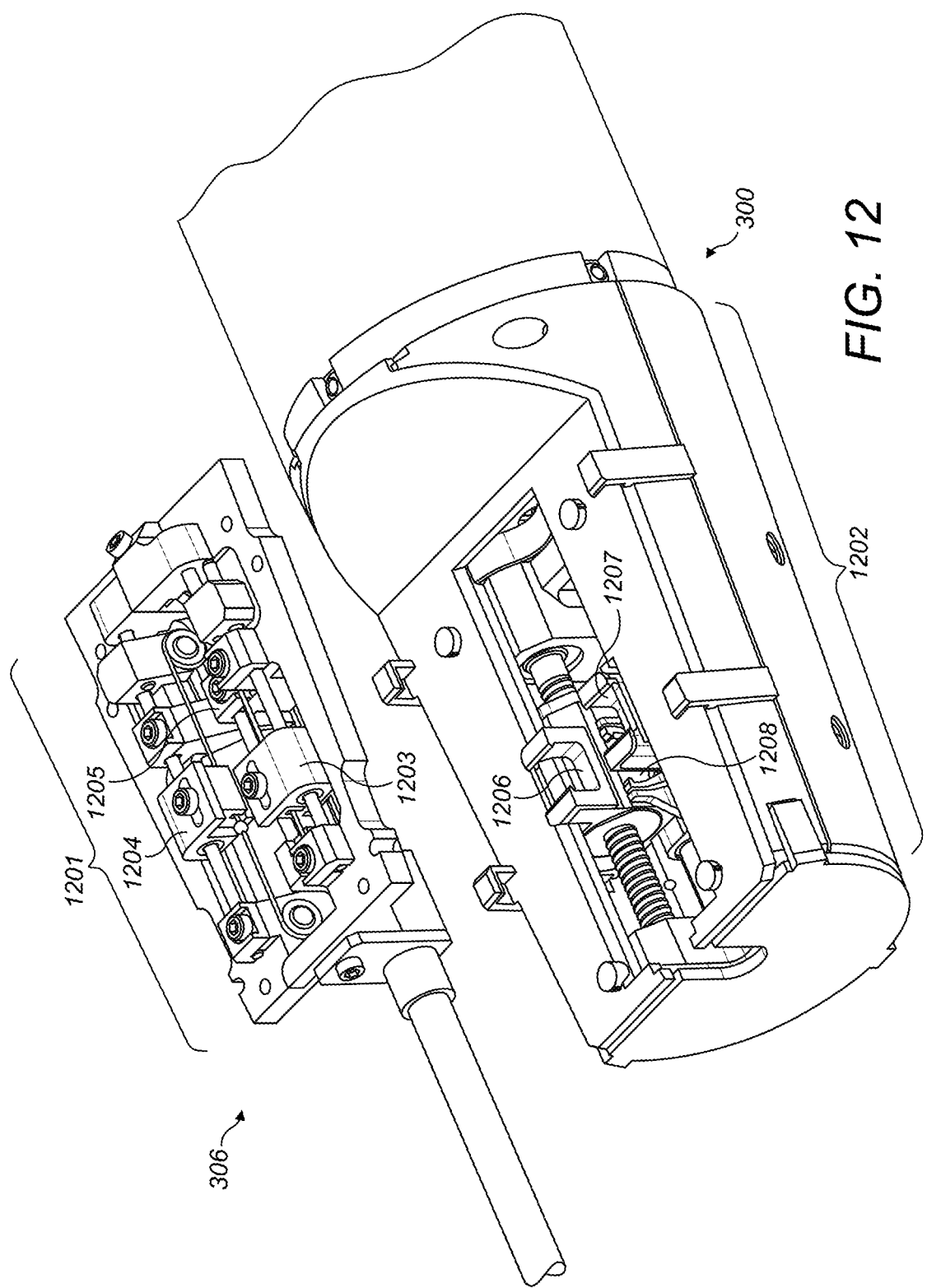
FIG. 12 illustrates an instrument being brought into engagement with a robot arm.

As described with respect to FIG. 3, suitably the robot arm terminates in a drive assembly. A drive assembly interface engages the instrument interface via movable drive assembly interface elements which drive movable instrument interface elements. FIG. 12 illustrates an exemplary mechanism by which a robot arm 300 engages with an instrument 306. In FIG. 12, instrument 306 is being brought into engagement with robot arm 300. Robot arm 300 terminates in drive assembly interface 1202. Instrument 306 terminates in instrument interface 1201. Instrument interface elements 1203, 1204 and 1205 are moveable within instrument interface 1201. The instrument interface elements are connected to driving elements in the shaft of the instrument. Those driving elements articulate joints at the distal end of the instrument. Drive assembly interface elements 1206, 1207 and 1208 are moveable within drive assembly interface 1202. The drive assembly interface elements 1206, 1207 and 1208 are moveable within drive assembly interface 1202.

The drive assembly interface elements 1206, 1207 and 1208 are driven by actuators of the robot arm 300. Each drive assembly interface element engages a respective instrument interface element. Drive assembly interface element 1208 engages instrument interface element 1205. Drive assembly interface element 1206 engages instrument interface element 1204. Drive assembly interface element 1207 engages instrument interface element 1203.

In an exemplary implementation, the proximity sensor 404 is located adjacent the drive assembly interface. The detectable tag 504 is located adjacent the surgical instrument interface. The relative locations of the proximity sensor 404 and the detectable tag 504 are selected such that when the surgical instrument is docked on the arm, the detectable tag 504 is proximal the proximity sensor 404. Thus, the proximity sensor detects the detectable tag when the instrument is docked on the arm. The locations of the proximity sensor and the detectable tag may be chosen such that if the instrument is not properly docked on the arm, the proximity sensor does not detect the detectable tag.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A surgical robot comprising:
   a base; and
   an arm having a proximal end and a distal end, the arm extending from the proximal end to the distal end via a series of links interspersed by articulations, the proximal end of the arm being attached to the base and the distal end of the arm being attachable to a surgical instrument, the arm comprising:
   a receiver configured to receive data transmitted from the surgical instrument over a short-range wireless communications link with the surgical instrument, the short-range wireless communications link using a radio frequency identification protocol; and
   a proximity sensor configured to detect a proximal presence of a detectable tag on the surgical instrument to the proximity sensor using a protocol which is different from the protocol used by the short-range wireless communications link; and
   a controller configured to respond to the proximity sensor detecting the proximal presence of the surgical instrument by enabling the short-range wireless communications link between the receiver and a transmitter of the surgical instrument to be established.

2. A surgical robot as claimed in claim 1, wherein the proximity sensor comprises a Hall sensor.

3. A surgical robot as claimed in claim 1, wherein the short-range wireless communications link is a Near Field Communications link.

4. A surgical robot as claimed in claim 1, wherein the data is indicative of the value of one or more parameters of the instrument.

5. A surgical robot as claimed in claim 4, wherein the parameters comprise surgical instrument type, surgical instrument identity, surgical instrument usage data, and control data.

6. A surgical robot as claimed in claim 1, further comprising a data store, the surgical robot configured to:
   receive data indicative of the surgical instrument identity;
   store the surgical instrument identity in the data store;
   subsequently receive a parameter update indicative of a surgical instrument identity and other parameter data; and
   only store the other parameter data of the parameter update if the surgical instrument identity of the parameter update matches the surgical instrument identity in the data store.

7. A surgical robot as claimed in claim 1, the receiver being comprised within an arm transceiver, and the transmitter being comprised within an instrument transceiver.

8. A surgical robot as claimed in claim 7, wherein the controller is configured to, in response to the short-range wireless communications link being established, control the arm transceiver to query the instrument transceiver over the short-range wireless communications link for the data.

9. A surgical robot as claimed in claim 7, wherein the arm transceiver is configured to periodically send data indicative of surgical instrument usage data to the instrument transceiver for storing in an instrument data store.

10. A surgical robot as claimed in claim 9, wherein the data indicative of surgical instrument usage data comprises data indicative of at least one of the total operation time of the surgical instrument, the number of uses of the surgical instrument, and the remaining lifetime of the surgical instrument.

11. A surgical robot as claimed in claim 7, wherein the proximity sensor is configured to detect that the surgical instrument has been detached from the arm, and wherein the controller is configured to respond to the detected detachment by controlling the arm transceiver to transmit data indicative of surgical instrument usage data to the instrument transceiver over the short-range wireless communications link.

12. A surgical robot as claimed in claim 11, wherein the controller is configured to only respond to the detected detachment by controlling the arm transceiver to transmit data indicative of surgical instrument usage data to the instrument transceiver over the short-range wireless communications link if the controller has not received a command indicating that the surgical instrument is to be detached from the arm.

13. A surgical robot as claimed in claim 1, wherein the controller is configured to prevent manipulation of the surgical instrument if the received data indicates that the instrument's lifetime has expired.

14. A surgical robot as claimed in claim 1, wherein the arm comprises a robot arm interface configured to mechanically interface a surgical instrument interface of the surgical instrument, and wherein the proximity sensor is located adjacent the robot arm interface.

15. A surgical robot as claimed in claim 1, further comprising a surgical instrument, the surgical instrument comprising:
   a transmitter configured to transmit data over the short-range wireless communications link to the receiver; and
   a detectable tag configured to be detectable by the proximity sensor.

16. A surgical robot as claimed in claim 15, wherein the detectable tag is detectable by a Hall sensor.

17. A surgical robot as claimed in claim 15, the receiver being comprised within an arm transceiver, and the transmitter being comprised within an instrument transceiver, wherein the surgical instrument further comprises a data store configured to store data indicative of surgical instrument usage data received from the arm transceiver.

18. A surgical robot as claimed in claim 15, wherein the arm comprises a robot arm interface configured to mechanically interface a surgical instrument interface of the surgical instrument, and wherein the proximity sensor is located adjacent the robot arm interface, wherein the surgical instrument comprises a surgical instrument interface configured to mechanically interface the robot arm interface, and wherein the detectable tag is located adjacent the surgical instrument interface proximal to the proximity sensor when the surgical instrument is attached to the arm.

19. A surgical robot comprising:
   a base; and
   an arm having a proximal arm and a distal end, the arm extending from the proximal end to the distal end via a series of links interspersed by articulations, the proximal end of the arm being attached to the base and the distal end of the arm being attachable to a surgical instrument, the arm comprising:
      a receiver configured to receive data transmitted from the surgical instrument over a short-range wireless communications link with the surgical instrument, the short-range wireless communications link using a radio frequency identification protocol; and
      a proximity sensor configured to detect a proximal presence of a detectable tag on the surgical instrument to the proximity sensor using a protocol which is different from the protocol used by the short-range wireless communications link; and
      a controller configured to respond to the receiver detecting a proximal transmitter operating according to the short-range wireless communications protocol and the proximity sensor not detecting the proximal presence of the surgical instrument by issuing an alert that the surgical instrument is not properly attached to the arm.

20. A surgical robot as claimed in claim 19, wherein the controller is further configured to respond to the receiver detecting a proximal transmitter operating according to the short-range wireless communications protocol and the proximity sensor not detecting the proximal presence of the surgical instrument by preventing manipulation of the surgical instrument.

* * * * *